United States Patent [19]
Friedmann

[11] Patent Number: 4,869,241
[45] Date of Patent: Sep. 26, 1989

[54] DISPOSABLE INTERNALLY APPLIED PENILE ERECTOR

[76] Inventor: John Friedmann, 4668 Venus St., New Orleans, La. 70122

[21] Appl. No.: 152,469

[22] Filed: Feb. 5, 1988

[51] Int. Cl.⁴ .............................................. A61F 5/00
[52] U.S. Cl. ...................................... 128/79; 128/842
[58] Field of Search ................ 128/79, 132 R, 138 R, 128/842, 843, 844; 604/328, 347, 349, 327

[56] References Cited

U.S. PATENT DOCUMENTS

| | | | |
|---|---|---|---|
| 3,446,206 | 5/1969 | DeLano | 128/79 |
| 3,463,141 | 8/1969 | Mozolf | 128/132 R |
| 3,987,789 | 10/1976 | Timm | 128/79 |
| 4,139,007 | 2/1979 | Diamond. | |
| 4,183,358 | 1/1980 | Cohen | 604/328 |
| 4,194,502 | 3/1980 | Eckels | 128/79 |
| 4,653,484 | 3/1987 | Cannon. | |
| 4,682,592 | 7/1987 | Thorsgard | 128/1 R |

FOREIGN PATENT DOCUMENTS 2444457 8/1980 France .......................... 128/132 R Primary Examiner—Robert Peshock
Assistant Examiner—Cary E. Stone
Attorney, Agent, or Firm—C. Emmett Pugh

[57] ABSTRACT

A disposable, internally applied penile erection aid having support means in the form of a hollow tube inserted into the urethra and having in combination therewith to hold the support tube in place comprising an exterior plastic or nylon member formed to fit over the head of the penis and latex sheath, formed to fit over the body of the penis. Another function of this invention is to aid in maintaining or prolonging an existing erection through the constriction of blood flow.

18 Claims, 2 Drawing Sheets

DISPOSABLE INTERNALLY APPLIED PENILE ERECTOR

BACKGROUND of INVENTION

1. Field of Invention

The present invention relates to devices and methods for facilitating sexual intercourse in males, and, more particularly, to penile erection aids temporarily applied to the user in a nonsurgical manner and easily removed.

2. Prior Art & General Background

Although distinguishable from the present invention, the prior art discloses a variety of devices comprising an external, portable means of attaining erection.

A list of prior patents which may be of interest is presented below:

| Pat. No. | Patentee(s) | Issue Date |
| --- | --- | --- |
| 3,446,206 | Artus D. DeLano | 05/27/69 |
| 3,987,789 | Jerald W. Timm | 10/26/76 |
| 4,139,007 | Harvey Diamond | 02/13/79 |
| 4,183,358 | Milton J. Cohen | 01/15/80 |
| 4,194,502 | John F. Eckels | 03/25/80 |
| 4,653,484 | Lamar J. Cannon | 03/31/87 |

As may be noted by a review of the above, the prior art teaches a variety of devices and methods for the support and erection of a penis. These devices have been generally divided into two categories: (1) surgically implanted devices, and (2) external splint members.

For an example of a surgically implanted prosthesis, note U.S. Pat. No. 3,987,789 (Timm et al) entitled "Malleable Penile Prosthesis." This patent teaches an elongated malleable rod portion which is housed within the generally tubular, physiologically inert plastic body. The rod is surgically implanted into the body of the penis, causing the penis to remain in an erectile state when desired, and afterwards the penis may be positioned and maintained by the prosthesis in a convenient, comfortable position by bending it into the desired position.

For an example of an externally applied penile support device, see U.S. Pat. No. 4,194,502 entitled "Externally Applied Support for a Penis." This patent discloses a curved base formed from a section of resilient tubular member having a first radius equal to the radius of the penis. The member is adapted to partially encircle and support the underside of the penis and merely attempts to work like an exterior partially encircling clamp.

U.S. Pat. No. 3,446,206 entitled "Surgical Splint" teaches another embodiment of an external, portable penile erection prosthesis. This device is in the form of a wire splint "having in combination therewith a penetrator means insertable into the outer end of the urethra of the male organ to stabilize the assembly under conditions of use." Though the curved tip of the device enters the urethra for mooring purposes, an external split along the exterior side of the penis is still required for penile rigidity.

Again, there is some doubt as to the effectiveness of this approach; the urethral stabilizing means apparently blocks the urethra of the penis; this blockage could effectually prevent ejaculation. Furthermore, the solid construction of the splint would appear to be rather uncomfortable for both the male and female partners. The bulbular or globe shaped object adjacent to the urethra opening of this device could cause damage or irritation to the urethra during the physical activities associated with the sex act. In comparison, the concave disk of the preferred embodiment of the present invention anatomically fits the rounded shape of the penis in a more natural, compatible manner. Also, the tubular member which creates the penile rigidity extends into the urethra to the base of the penis requiring no exterior splint to obtain penile erection.

3. General, Summary Discussion of the Invention

The present invention teaches a new and unobvious device and method of providing for a penile erection, which is both effective, yet inexpensive, and which does not rely on surgical implantation. In lieu of the exterior splints and/or other means of providing for non-surgical erection, the present invention relies upon supporting the penis from within, that is, the use of a supporting, semi-rigid tubular member into the urethra of the penis, and incorporating means to comfortably hold the supporting member in place.

This holding means preferably comprises the utilization of a hemispherical and anatomically correct concave, disc affixed to the exterior portion of the tubular supporting member, with the disc shaped and sized to fit over the head of the average penis. The disc prevents the splint from being inserted too deeply into the urethra. Furthermore, the disc is affixed to the supporting member in such a manner as to allow the hollow member to remain unblocked, so that bodily fluids may be discharged through the penis at the time of ejaculation. An alternative embodiment teaches a design utilizing a latex reservoir over the discharge port, thus preventing semen from being discharged into the partner.

In order to further facilitate a comfortable and effective positioning of the support tubing and in order to facilitate continued erection, the preferred embodiment of the present invention teaches the utilization of a latex or elastic rubber sleeve, much like a condom, affixed to the disc, in such a manner as to allow the sleeve to be slid over the penis in order to keep the splint in place.

In order to use the device, one merely slides the support tubing down the urethra of the user's penis until the concave disc at the end of the hollow support tube touches the head of the penis. The elastic rubber sleeve is then rolled over the penis much like one applies a condom. At this point, the device is completely installed and the user is ready for intercourse.

The elastic sleeve, in addition to supporting the hollow tubular member, also has the effect of restricting the flow of venal blood out of the penis. This assists in the retention of blood in the corpora cavernosa of the penis by the tightness of the latex sleeve at the base of the penis. Thus an erection may be sustained in a similar fashion to a normal erection.

As may be ascertained by a comparative review of the prior art, the present invention teaches a new and unobvious device and method of maintaining penile erection. The use of the urethra as an area of support offers a perfect open area inside of the penis in which to place a splint, which in turn provides rigidity to the penis. Further, the use of the urethra for insertion of the splint in conjunction with the anatomically correct, disc "mooring" and condom-like latex or rubber sleeve also assures that there will be no injury to the male or female involved in sexual intercourse.

Another feature of this invention is that the user continues to have an enhanced cosmetic appearance quite similar to the natural penis, rather than the exterior wire-splint arrangements as taught in the prior art. With the present invention, the appearance is more that of a penis with a condom placed over it, rather than an externally applied splint.

Another feature of this invention is that the device may be disposable and thus offer sanitary advantages over the prior art. One could use the device much as one would use a condom, purchasing the item in a sealed package, using it once, and then disposing of it.

As the device would be relatively inexpensive to manufacture, the price factor makes it feasible to use a new penile erector each time sexual intercourse takes place. The prior art, which makes use of wire or tubular splints for external penile erection devices must be thoroughly cleansed after each use. The prior art teaches that this must be done in order to prevent bacterial or viral build-up after use from either the sex partner or the environment in general.

With the well known venereal diseases and the much more recent threat of the HIV or AIDS virus, the disposable feature of the present embodiment lends itself to a much safer environment for the sexual act.

BRIEF DESCRIPTION of the DRAWINGS

For a further understanding of the nature and objects of the present invention, reference should be had to the following detailed description, taken in conjunction with the accompanying drawings, in which like parts are given like reference numerals, and wherein:

FIG. 5 is a side view of a further preferred embodiment of the present invention illustrating an alternative embodiment, similar to the embodiment of FIG. 2, but incorporating a latex reservoir over the front, centrally located, discharge port of the concave disc, preventing discharge of the semen for birth control/disease control and/or other purposes.

DETAILED DESCRIPTION of the PREFERRED, EXEMPLARY EMBODIMENTS

Figure 1:
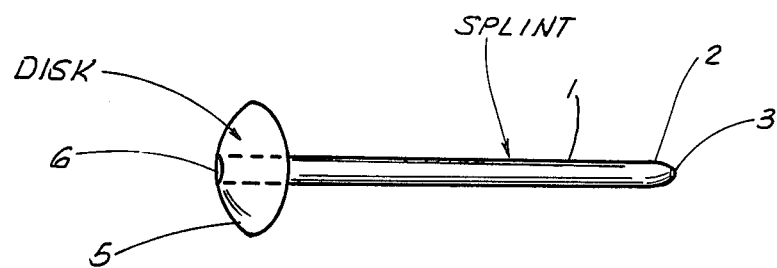
FIG. 1 is a side view of a first, simplified, exemplary embodiment of the present invention, in which the device does not incorporate a latex sleeve or reservoir. This embodiment would be used in conjunction with an off-the-shelf condom.

As may be seen in FIG. 1, the first exemplary embodiment of the present invention includes a hollow, tubular support or splint member 1, open at both of its ends.

The tube 1 can be for example approximately three-sixteenths of an inch in diameter and three and a half to five inches long as a typical size. Customized or other typical sizes can be determined by, for example, consultation with a physician and depends upon the length of the penis of the user. The hollow tubular member is preferably constructed of a sanitary, physiologically inert, pliable yet firm and relatively inexpensive material, such as for example plastic.

The tube 1 tapers off slightly from area 2 of the tube 1 to opening 3. The material comprising the tapered off portion of tube 1, that is from area 2 to tip 3 should be somewhat more pliable and correspondingly less rigid than the rest of the tube 1. The purpose of this softer material would be to help prevent damage to the urethra upon insertion and/or during intercourse. The more pliable material might consist of, for example, latex rubber.

An alternative embodiment could comprise a tube without a tapered tip 3, but still having the more pliable, softer material for one-quarter inch from the tip 3, for example. Nonetheless, tip 3 should be rounded smoothly for example as smooth as a water glass edge for easier insertion. The tube's 1 width should be sized by a physician to meet individual needs and to prevent discomfort.

A concave disc 5 is permanently affixed to and around the external, outer tip end of the support member 1. The disc 5 is configured in such a manner as to contour to and follow the configuration of the head of the average or typical penis and can be, for example, approximately three-quarters of an inch in diameter. The back or underside of the disc 5 can be seen in FIG. 4.

The center of the disc 5 includes an opening 6, which in conjunction with the distal end opening 3 and the hollow structure of the tube 1 allows communication from the urethra through the hollow support member and ultimately through the concave support disc 5 for possible external discharge of the semen. Like the support member 1, the disc 5 should be made of a firm yet relatively pliable and inexpensive material.

Figure 2:
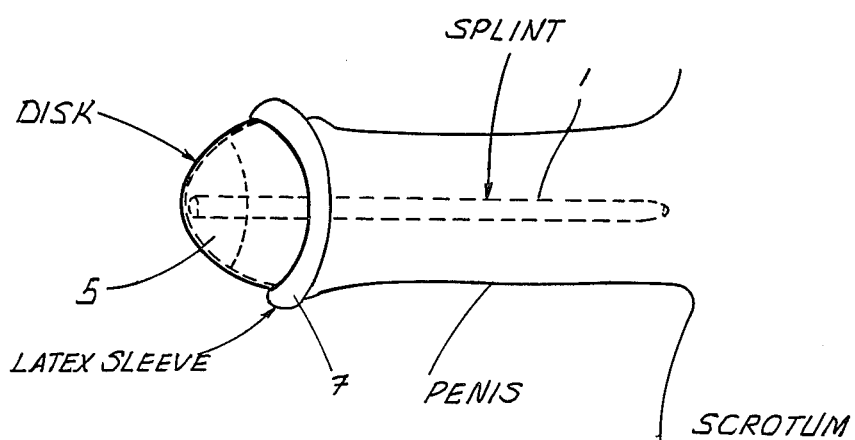
FIG. 2 is a side view of the preferred embodiment of the present invention showing the support member tube in phantom slidably placed into the urethra of the penis, the concave button-cap configuration at the head of the penis, and the latex or rubber sleeve in a reversed, rolled up disposition, as it would be just prior to application of the sleeve over the penis, thus completing installation of the device.

As is illustrated in FIG. 2, in a further embodiment a tubular, latex or rubber "sleeve" 7 is permanently affixed around the periphery of disc 5, in such a manner as to allow the sleeve to be rolled out over the length of the penis in similar fashion to that for a condom. However, when in place, the sleeve 7 also acts in such a manner as to exteriorly support the internal positioning of the urethral support member 1 and keeps and maintains the entire device in place.

Figure 3:
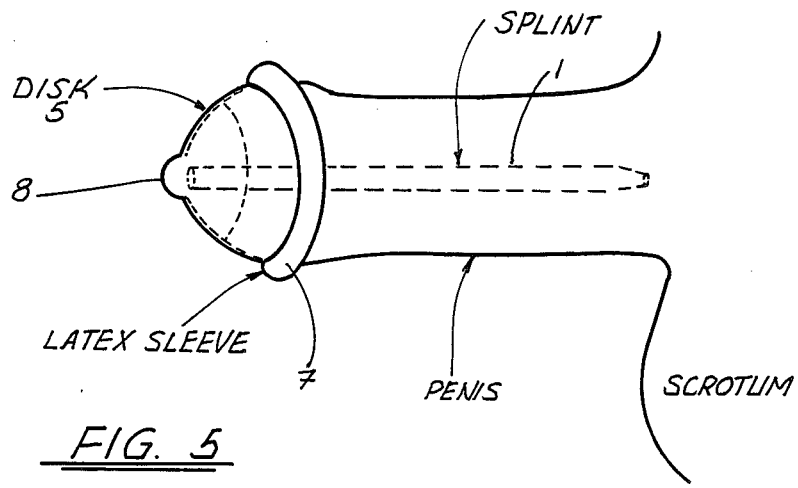
FIG. 3 is a side view of the preferred embodiment of the present invention fully installed within the urethra, with the covered penis shown and the inserted tubular support member shown in phantom line.
Figure 3:
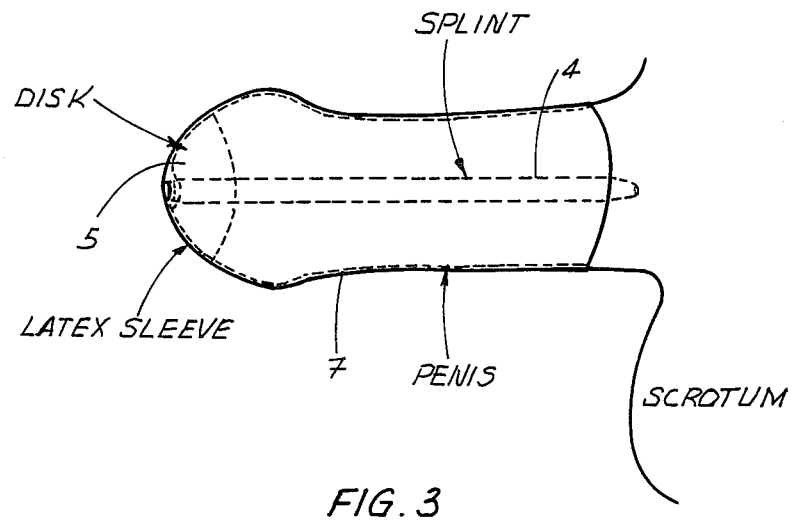
Figure 4:
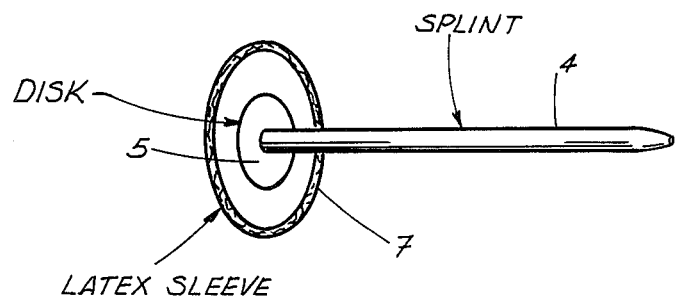
FIG. 4 is a rear, perspective view of the preferred embodiment of the present invention showing the device (and the underside of the hemispherical concave disc) in its pre-use state without the wrapping, with the latex sleeve rolled up and at the peripheral, round edge of the concave disc.

As can be seen in FIGS. 2 & 4, the sleeve 7 is initially rolled up but, as can be seen in FIG. 3, is thereafter rolled out over the exterior of the penis when the device is fully applied to the penis. As opposed to the complete, initial state of the sleeve 7 shown in FIG. 4, the sleeve 7 has been rolled out a small amount just over the head of the penis in its disposition shown in FIG. 2.

The elastic sheath 7 can have the same thickness, elasticity and dimensions of a condom, yet, as discussed above, would be permanently affixed to the concave disc 5 at and around its periphery, but not necessarily covering the central disc and tube opening 6. Thus, at least with regard to this exemplary embodiment, the sheath 7 would not act as a means of birth control.

However, it is noted that in a further alternative embodiment, illustrated in FIG. 5, the sheath 7A includes a hemispherical central reservoir 8 over the opening 6 for birth control and the like, if such is so desired. However, in other respects, the sheath 7A can be substantively identical to the sheath 7 of the embodiment of FIG. 2.

Thus, in summary, in an initial, relatively simple embodiment, the erection device could comprise merely the hollow tubular support member 1 and the concave disc 5. This embodiment is illustrated in FIG. 1. In lieu of the permanently affixed latex sheath or sleeve 7, the initial embodiment would be used in conjunction with an off the shelf condom. The device would be used the same as with the more preferred embodiments, that is, the support member 1 is slidably placed in the urethra of the user until the concave disc 5 touches the head of the penis. At that point, an off the shelf condom would be placed over the concave disc 5 and the head of the penis, and thereby rolled over the entirety of the penis, thus acting in itself as would have latex sheath 7; any off-the-shelf condom should be tight enough to be secure the disc in place; additionally, this alternative embodiment allows the practice of birth control in conjunction with the erection system of the present invention.

In a similar embodiment, the latex sheath would comprise essentially a condom permanently affixed to concave disc 5, having a reservoir 8 over the discharge port 6. This embodiment is illustrated in FIG. 5 of the drawings.

As noted above, the tubular member may vary in length depending upon the length of the user's penis.

Another feature of the support member 1 is that it can be lubricated for easy and painless insertion into the urethra. The lubricant should be water based in order to prevent any possible corrosive breakage of the latex sleeve and/or reservoir which accepts the semen. While a preferred embodiment of the present invention has been described, it should be understood that various changes, adaptations and modifications may be made therein without departing from the spirit of the invention and the scope of the appended claims.

The embodiment(s) described herein in detail for exemplary purposes are of course subject to many different variations in structure, design, application and methodology. Because many varying and different embodiments may be made within the scope of the inventive concept(s) herein taught, and because many modifications may be made in the embodiment(s) herein detailed in accordance with the descriptive requirements of the law, it is to be understood that the details herein are to be interpreted as illustrative and not in a limiting sense.

What is claimed is:

1. An internally applied penile erector prothesis for treating erectile impotence, comprising:
   a tubular, elongated support member, having a tip and dimensions substantially equal to that of the urethra and length substantially equal to that of the body of the penis to which the device is to be applied and designed to be slidably placed in the urethra of the use providing an internal means of support of the user's penis, said internal means of support aiding in the erection of the penis; and
   a generally circular, concave, anatomically correct disc permanently attached to said tip of said tubular support member, having dimensions such that it partially covers the head of the penis.

2. The erector prothesis of claim 1, wherein said tubular support member comprises a physiologically inert, rigid yet somewhat elastic material.

3. The erector prothesis of claim 1, wherein said concave disc comprises a physiologically inert material.

4. The erector prothesis of claim 1, wherein said circular, concave, anatomically correct disc has a distal end opening discharging any fluids which may pass through said tubular support member.

5. An internally applied penile erector prothesis for treating erectile impotence, comprising:
   a tubular, elongated support member, having a tip and dimensions substantially equal to that of the urethra and length substantially equal to that of the body of the penis to which the device is applied and designed to be slidably placed in the urethra of the user providing an internal means of support of the user's penis, said internal means of support aiding in the erection of the penis;
   a generally circular, concave, anatomically correct disc permanently attached to said tip of said tubular support member, having dimensions such that it partially covers the head of the penis; and
   an elastic sheath, said sheath having one end permanently affixed around the periphery of said concave disc.

6. The erector prothesis of claim 5, wherein said tubular support member comprises a physiologically inert, rigid yet somewhat elastic material.

7. The erector prothesis of claim 5, wherein said concave disc comprises a physiologically inert material.

8. The erector prothesis of claim 5, wherein said circular, concave, anatomically correct disc has a distal end opening discharging any fluids which may pass through said tubular support member.

9. The erector prothesis of claim 5, wherein said sheath has dimensions and length substantially that of the body of the penis to which the device is applied.

10. The erector prothesis of claim 5, wherein said sheath comprises a material having plastic properties.

11. An internally applied penile erector prothesis for treating erectile impotence, comprising:
   a tubular, elongated support member, having a tip and dimensions substantially equal to that of the urethra and length substantially equal to that of the body of the penis to which the device is to be applied and designed to be slidably placed in the urethra of the user providing an internal means of support of the user's penis, said internal means of support aiding in the erection of the penis;
   a generally circular, concave, anatomically correct disc permanently attached to said tip of said tubular support member, having dimensions such that it partially covers the head of the penis, said circular, concave, anatomically correct disc having a distal end opening discharging any fluids which may pass through said tubular support member;
   a reservoir enveloping said distal end opening of said anatomically correct disc restricting the flow of fluids from said distal opening; and
   an elastic sheath, said sheath having one end permanently affixed around the periphery of said concave disc.

12. The erector prothesis of claim 11, wherein said tubular support member comprises a physiologically inert, rigid yet somewhat elastic material.

13. The erector prothesis of claim 11, wherein said concave disc comprises a physiologically inert material.

14. The erector prothesis of claim 11, wherein said reservoir comprises a material having elastic properties.

15. The erector prothesis of claim 11, wherein said sheath has dimensions and length substantially that of the body of the penis to which the device is applied.

16. The erector prothesis of claim 11, wherein said sheath comprises a material having elastic properties.

17. A method of utilizing a tubular support member slidably applied into the urethra of the penis in order to provide support for that penis in simulating, enhancing or maintaining an erection, comprising the following steps:
   (a) slidably placing a hollow, tubular, elongated support member having a tip and a length substantially equal to that of the penis to which the device is applied into the urethra of the user in order to stimulate, enhance, or maintain an erection;
   (b) utilizing a generally circular, concave, anatomically correct disc permanently attached to the tip of the tubular support member, having dimensions such that it partially covers the head of the penis enhancing support and preventing the support member from being placed too far into the urethra, and having a distal end opening for allowing communication of fluids from the hollow, tubular support member through the distal end only; and
   (c) then applying a prophylactic condom over the length of the penis installed with the penile erector holding the erector prothesis in place.

18. A method of utilizing a tubular support member slidably applied into the urethra of the penis in order to provide support for that penis in simulating, enhancing or maintaining an erection comprising the following step(s):
   (a) slidably placing a hollow, tubular, elongated support member having a tip and a length substantially equal to that of the penis to which the device is applied in to the urethra of the user in order to stimulate, enhance, or maintain an erection;
   (b) utilizing a generally circular, concave, anatomically correct disc permanently attached to the tip of the tubular support member, having dimensions such that it partially covers the head of the penis enhancing, supporting and maintaining an erection and preventing the support member from being placed too far into the urethra, and having a distal end opening allowing communication of fluids from the hollow, tubular support member through the distal end; and
   (c) utilizing an elastic sheath having dimensions and length substantially equal to that of the penis to which the device is applied, said sheath being permanently attached at one end to the disc further stabilizing the penile erector and further enhancing erection.

* * * * *